US008776558B2

(12) United States Patent
Volker

(10) Patent No.: US 8,776,558 B2
(45) Date of Patent: Jul. 15, 2014

(54) SYSTEM FOR ULTRASONICALLY DETECTING DEFECTS IN A PIPE WALL

(75) Inventor: Arno Willem Frederik Volker, Delft (NL)

(73) Assignee: Nederlandse Organisatie voor Toegepast-Natuurwetenschappelijk Onderzoek TNO, Delft (NL)

( * ) Notice: Subject to any disclaimer, the term of this patent is extended or adjusted under 35 U.S.C. 154(b) by 917 days.

(21) Appl. No.: 12/934,504

(22) PCT Filed: Mar. 25, 2009

(86) PCT No.: PCT/NL2009/050144
§ 371 (c)(1),
(2), (4) Date: Dec. 8, 2010

(87) PCT Pub. No.: WO2009/120076
PCT Pub. Date: Oct. 1, 2009

(65) Prior Publication Data
US 2011/0087444 A1 Apr. 14, 2011

(30) Foreign Application Priority Data
Mar. 25, 2008 (EP) .................... 08153225

(51) Int. Cl.
*G01N 29/04* (2006.01)
(52) U.S. Cl.
CPC ..................... *G01N 29/04* (2013.01)
USPC .......................................................... 70/39
(58) Field of Classification Search
USPC .......................................... 702/39
See application file for complete search history.

(56) References Cited

U.S. PATENT DOCUMENTS

| 6,848,313 | B2 | 2/2005 | Krieg et al. |
| 2003/0061880 | A1 | 4/2003 | Bazarov et al. |
| 2003/0136195 | A1 | 7/2003 | Krieg et al. |
| 2006/0219011 | A1 | 10/2006 | Siddu et al. |
| 2009/0078742 | A1 * | 3/2009 | Pasquali et al. ............... 228/103 |

FOREIGN PATENT DOCUMENTS

| EP | 0251698 A2 | 1/1988 |
| EP | 1333277 A2 | 8/2003 |
| EP | 1707956 A2 | 10/2006 |
| RU | 2 194 274 C1 | 12/2002 |

(Continued)

OTHER PUBLICATIONS

Jian Ma, On-Line Measurements of Contents Inside Pipes Using Guided Ultrasonic Waves, Oct. 2007, pp. 1-193.*

(Continued)

*Primary Examiner* — Tung S Lau
(74) *Attorney, Agent, or Firm* — Birch, Stewart, Kolasch & Birch, LLP

(57) ABSTRACT

A system for detecting defects in a pipe wall, comprises an ultrasonic transducer which is arranged for emitting, via an exit opening, ultrasonic signals from the interior of the pipe towards its wall and for receiving, via an entrance opening, backscattered signals from the wall. The system is arranged to emit and receive a multitude of signals having their main directions within a plane mainly perpendicular to the pipe axis. The openings are configured to make the ultrasonic transmission signal diverge and/or to receive back signals from a diverging range of angles over a large area of the pipe wall, by using openings with a diameter with magnitude of the wavelength of the ultrasonic signals. Sets of emitted and backscattered signals for different emission and reception positions are processed, in processing means, to form an image based on transmission times between emission and reception of backscattered signals.

18 Claims, 1 Drawing Sheet

(56) References Cited

FOREIGN PATENT DOCUMENTS

| RU | 2 205 396 C1 | 5/2003 |
|---|---|---|
| WO | WO 96/13720 A1 | 5/1996 |
| WO | WO 2008/010711 A1 | 1/2008 |

OTHER PUBLICATIONS

Jaiwan Cho, Defect Detection Within a Pipe Using Ultrasound Excited Thermography, Sep. 19, 2007, pp. 637-646.*

R. Kays, Detection of defects in multi-layered plastic cylindrical structures by ultrasonic method, Published in Ultragarsas Journal 2002 vol. 43 No. 2, 4 pages.*

Berkhout, "Applied Seismic Wave Theory", Elsevier Science Publishers B.V., 1987, pp. 1-197.

E. Luiten, "Verbeterde afbeeldingstechnieken voor ultrageluid pigs," or as translated in English on p. 8 of the Specification as, "Improved imaging techniques for ultrasound," TNO-report IS-RPT-060054, Delft., TNO Industrie en Techniek, Feb. 17, 2006, pp. 1-89.

* cited by examiner

SYSTEM FOR ULTRASONICALLY DETECTING DEFECTS IN A PIPE WALL

FIELD OF THE INVENTION

The invention concerns a method and system for detecting defects in a pipe wall, comprising an ultrasonic transducer arranged for emitting, via an exit opening, ultrasonic signals from the interior of the pipe towards its wall and for receiving, via an entrance opening, backscattered signals from its wall.

BACKGROUND

Prior art ultrasound systems, sometimes referred to as (detection) "pigs", comprise one ultrasound transducer and a mirror, via which the sound is directed towards the pipe wall. The same transducer receives the backscattered echoes from the pipe wall. This prior art technique has some limitations, e.g.:
  the alignment of the transducer has to be nearly perfect; otherwise the echoes will not be detected;
  the surface of the pipe wall needs to be smooth; otherwise the signal gets unusable;
  cracks and corrosion pitting are not detected.

EP1707956 discloses a method and system for detecting the depth of cracks in a pipe. The system involves a pig that is configured to send ultrasonic signals circumferentially in the pipeline walls and to receive reflected signals. The document describes an example wherein multiple sensors are located around the pig and arranged to transmit ultrasonic signals that strike the pipeline wall at a certain angle. The surfaces of the pipe wall as well as cracks in the wall act as ultrasonic reflectors that produce reflections at various delay times.

Reflections from the surfaces of the wall repeat at so-called skip distances, dependent on wall thickness. Reflections from cracks can be distinguished because they are received with other delays. The distance to the reflector is determined from the delay time and ultrasonic ray tracing to simulate the path of the reflections. The distance to the reflectors is used to estimate crack depth. The maximum among the depths determined from different sensors is used as estimated depth of the crack.

This known system merely determines the depths of individual cracks. It does not attempt to use an imaging process to form an image of the pipe wall. Furthermore, the known system relies on directional sensors, which produce rays that strike the pipeline wall at a known angle. This makes it possible to use ray tracing to determine the depth.

It has been found that in practice the surface of the pipe wall may be uneven, with erratic thickness variations due to corrosion and wear, not just with isolated cracks. Due to the sizeable sound speed differences between the pipe wall and the fluid within the pipe, the unevenness results in considerable scattering of the ultrasonic rays at unpredictable angles. This would make imaging with the system of EP1707956 very unreliable in pipes that suffer from corrosion and wear.

SUMMARY

Among others it is an object to provide for improved pipe inspection

A method according to claim 1 and a system according to claim 8 are provided. Herein a multitude of ultrasonic signals are emitted and received having their main directions within a plane mainly perpendicular to the longitudinal direction of the pipe axis. The emitted and backscattered signals are processed using a high resolution imaging process based on the transmission time of the emitted and backscattered signals. The imaging process forms an image, for example of backscatter intensity as a function op position in said plane. Preferably each signal of the multitude is emitted and/or received at angles distributed over the plane. Preferably, the diameter of said exit and/or entrance opening used for emission and/or reception are selected sufficiently small in relation to the emission frequency of transducer, at which the transducer transmits ultrasonic signals, so that ultrasonic transmission signal from each opening diverges to a rather large area of the pipe wall and/or each opening receives each backscattered from a rather large area of the pipe wall. This may be realized for example by using exit and/or entrance openings that have a diameter of the magnitude of the wavelength of the ultrasound, for example a diameter in the circumferential direction of no more than twice the wavelength of ultrasound in the fluid in the pipe at the sound emission frequency of the transducer. The openings may have a larger diameter in the axial direction.

In an embodiment the signals are processed by applying Fermat's principle, which states that the path taken between two points by a sound ray is the path that can be traversed in the least time. The application of Fermat's principle may comprise determining the transmission times associated with a set of paths from and/or to a transducer and selecting a path that has a smallest transmission time. It has been found that this provides a more robust solution to handle the unevenness of pipe walls that results from corrosion and wear. This applies advantageously to an embodiment wherein an estimate of the location of the surface of the pipe wall is used to process the signals to obtain an image of the interior of the pipe wall.

In an embodiment
  sound transmission and sound speed in a homogeneous medium within the pipe is taken into account as well as:
    the sound transmission and sound speed within the pipe wall,
    the refraction of sound on the boundary between the medium within the pipe and the pipe wall, and
    the reflections within the pipe wall;
  sound transmission paths within the pipe as well as within the pipe wall are determined efficiently and effectively applying Fermat's principle, stating that the path taken between two points by a sound ray is the path that can be traversed in the least time;
  an image of the pipe wall is presented in order to facilitate a visual interpretation of the measurement results.

Arranging the array of transducers to emit and receive a multitude of signals in a multitude of directions mainly perpendicular to the pipe axis, in combination with using transducers having exit/entrance openings in the order of magnitude of the used ultrasound wavelength, will cause the ultrasonic transmission signal to diverge and to reflect or backscatter on a rather large area of the pipe wall. The transducers in the array may be applied simultaneously or sequentially. Because the sound reflects (backscatters) in a large area, the complex of emitted and backscattered signals can (and should) be put to a high resolution imaging process, based on the transmission time of the emitted and backscattered signals, in order to get everything on the right spot in a detailed image which can be made of the cross-section (corresponding with the plane mainly perpendicular to the pipe axis. It is noted here that high resolution imaging processes are of general knowledge as such in various arts, e.g. within the field of medical (ultra)sonography and in seismic exploration [A. J. Berkhout. *Applied seismic wave theory*. ISBN 0-444-42898-4. Elsevier Science Publishers B.V., 1987].

The imaging steps preferably comprise:
a. Imaging of data with a model that includes only the liquid velocity (taking into account the sound speed in the liquid within the pipe), using in particular reflections from the pipe's inner surface.
b. Finding the pipe's inner surface.
c. Update the velocity model, including the sound speed in the pipe wall in the model.
d. Image the pipe wall, its inner and its outer surface, and peculiarities like defects in the pipe wall.

Imaging the pipe wall, its inner and its outer surface and peculiarities like defects in the pipe wall, preferably involves:
a. Defining a grid of points within the pipe wall.
b. Calculating for each grid point the sound transmission time for the sound path between each pair of emitting element and receiving element, via said grid point.
c. Determining for each grid point the sum of the responses, corresponding with the calculated sound transmission times, applying true amplitude weights of the emitted and backscattered signals.

If a grid point corresponds to a sound scattering part of the pipe wall, the weighted sum of the responses will get a clearly nonzero value (with a level above noise level). Conventionally, sound transmission times are calculated applying ray tracing techniques. According to one aspect, it is preferred that sound transmission times are determined more efficiently applying Fermat's principle, by choosing a set of neighbouring sound transmission paths, calculating the corresponding sound transmission times and selecting the sound path with the shortest travel time.

The advantages of the disclosed measurement method are:
insensitivity for normal alignment errors;
high resolution, enabling detecting small defects;
insensitivity for surface irregularities.

BRIEF DESCRIPTION OF THE DRAWING

These and other object and advantageous aspect will become apparent from a description of exemplary embodiments using the following figures.

DETAILED DESCRIPTION OF EXEMPLARY EMBODIMENTS

Figure 1:
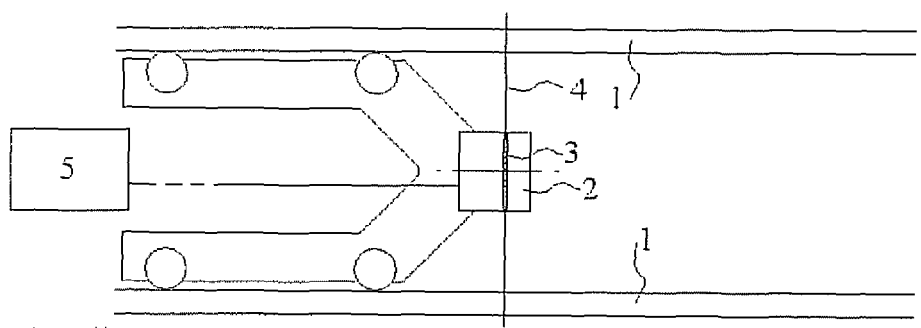
FIG. 1 shows a first embodiment of the system

FIG. 1 shows an exemplary embodiment of a system for detecting defects in a pipe wall 1, comprising ultrasonic transducers 2 which are arranged for emitting, via an exit opening, ultrasonic signals from the interior of the pipe towards its wall 1 and for receiving, via an entrance opening, backscattered signals from its wall 1. In this exemplary embodiment the transducers comprise a mainly circular array of ultrasonic transducers 3, arranged to emit and receive a multitude of signals having their different main directions within a plane 4 mainly perpendicular to the pipe axis. The transducers 3 are connected with a control module 5 which is arranged to energize the transducers 3 to emit their signals, i.e. signal pulses. Those signal pulses can be emitted simultaneously or sequentially or mixed. The backscattered signal pulses can be received by the same transducers in the time slots (reception slots) between the time slots (emission slots) in which the signal pulses are emitted towards the pipe wall. The backscattered signal pulses are transmitted to the control module 5 and processed there or in other processor.

As used herein a "processor" may be a programmable processor programmed with a program (e.g. in memory or on disk) to perform the operations as described. Instead a processor may be circuit that is hardwired to perform these operations. The processor may comprise a plurality of sub-processors to perform respective tasks of these operations.

The diameter of the exit openings (for pulse emission) and entrance openings (for pulse reception) of the transducers mainly have the magnitude of the wavelength of the used ultrasonic signals, which causes the signal pulses to diverge and thus to irradiate a rather large area of the pipe wall and to be susceptible for various kinds of defects in the pipe wall.

In an embodiment each transducer is implemented as a body of piezoelectric material that can act both as an emitter, when an electric field is applied to it, or as a receiver, when the electric field generated by the body is detected. In this embodiment the exit openings and entrance opening of the transducer may be defined by the body. Thus, the diameter of the exit opening and entrance opening may correspond to the diameter of the body of piezoelectric material. A circular array of such bodies may be provided along the circumference of a cylinder, for use within the pipe. In another embodiment, a plurality of transducers may be realized on a single body of piezoelectric material, with a plurality of electrode pairs facing the body at respective locations, each pair defining the exit opening and entrance opening of a respective transducer.

Preferably, the diameter of the exit opening and entrance opening in the circumferential direction of the pipe is at most twice the wavelength of the ultrasonic signal in the pipe. A diameter of between half and two wavelengths may be used for example, or between a half and one wavelength. Thus substantially omnidirectional ultrasound radiation may be realized distributed over the radial directions perpendicular to the axial direction of the pipe. The diameter of the exit opening and entrance opening in the axial direction of the pipe may be larger, for example at least five wavelengths, in order to provide for radiation concentrated substantially in a plane perpendicular to the axial direction of the pipe.

The emitted and backscattered signal pulses, including their delay/transmission times) is processed in the processing module or further processing/computing means, using a well suited high resolution imaging process, e.g. the process described in E. Luiten TNO-report IS-RPT-060054. Delft, 17 Feb. 2006. *Verbeterde afbeeldingstechnieken voor ultrageluid* (*Improved imaging techniques for ultrasound*; in Dutch).

Briefly summarized, such a process provides for the generation of an image using tomographic techniques. As used herein, an image comprises image values associated with spatial locations distributed over an at least two dimensional area. By means of signals obtained when the transducer arrangement is at an axial position in the pipe, a two dimensional image of image values in a plane perpendicular to the axis of the pipe may be obtained, for example as a function of radial distance from the axis of the pipe and circumferential angle around the axis of the pipe. By means of repeated measurements at different axial locations along the pipe a three dimensional image may be obtained.

In the case of emitted and backscattered signal pulses, the image values represent backscatter intensity from spatial locations. An individual backscatter signal, from an opening of the transducer and back to an opening, provides backscatter intensity as a function of time. For any one time this backscatter intensity is a sum of contributions of backscatter intensities from a set of spatial locations that result in the same delay time of ultrasound propagation to and from the location via the openings. A delay time can be assigned to each combination of an emitting transducer, a pixel location in such an image, and a receiving transducer. The assigned delay time is the delay time between emission and reception of an ultrasonic signal that is emitted by the emitting transducer, reflected by material at a pipe location corresponding to the pixel location, and received by the receiving transducer. Thus, when the reflection amplitude signal as a function of time is considered for a combination of an emitting transducer and a receiving transducer, each time point corresponds to a set of pixel locations in the image with assigned delay times equal to the time value of that time point.

Tomographic techniques use a plurality of such combinations of an emitting transducer and a receiving transducer to realize spatial resolution of the backscatter intensity. In the process described by Luiten this corresponds to computation of backscatter intensity for spatial locations that correspond to image locations, each by determining the delay times associated with that spatial location for each combination of an emitting transducer and a receiving transducer and summing the backscatter signals for those combinations at those delay times. As a result an image of computed backscatter intensities as a function location is produced.

In an embodiment, a computation with a first and second pass is used. This is because the delay times associated with spatial locations within the pipe wall depend on the shape of the pipe wall, which may be unpredictable due to corrosion and wear. Accordingly, a first pass is used wherein a first backscatter intensity image is computed under the assumption that ultrasound propagation speed does not depend on spatial position. Of course, this assumption does not correspond to reality, because the ultrasound propagation speed in the fluid in the pipe and in the pipe wall are strongly different. However the first backscatter intensity image does provide information that makes it possible to determine the position of the inner surface of the pipe wall. This makes it possible to perform a second pass, wherein a second backscatter intensity image is computed under the assumption that ultrasound propagation speed has a first and second value, corresponding to speed in the fluid and the pipe wall, inside and outside the inner surface that was determined from the first image respectively. Optionally, further passes like the second pass may be used, wherein the second image produced by a previous pass takes the place of the first image.

Accordingly, the process preferably comprises:
a. computing a first image using a sound velocity model (e.g. values of the sound velocity as a function of spatial location) that includes only the liquid velocity for all positions (taking into account the sound speed in the liquid within the pipe), using in particular reflections from the pipe's inner surface.
b. Finding the pipe's inner surface from the first image.
c. Update the velocity model, including in the model the sound speed in the pipe wall bounded by the inner surface as found from the first image.
d. computing a second image using the updated model to image the pipe wall, its inner and its outer surface, and peculiarities like defects in the pipe wall.

Computing the second image of the pipe wall, its inner and its outer surface and peculiarities like defects in the pipe wall, preferably involves:
a. Defining a grid of points within the pipe wall.
b. Calculating for each grid point and for each pair of an emitting element and a receiving element the sound transmission time along the sound path from the emitting element in the pair to the receiving element in the pair, via reflection from said grid point.
c. Determining for each grid point the sum of the backscatter responses determined with different ones of the pairs at the calculated sound transmission times for the pairs. Optionally amplitude weights may be applied in the determination of the sum.

If a grid point corresponds to a sound scattering part of the pipe wall, the weighted sum of the responses will get a clearly nonzero value (with a level above noise level).

In this way, the computation of the second image is dependent on the inner surface of the pipe wall that has been found from the first image. Thus, the position of the inner surface and therefore the sound transmission time does not have a predetermined value. It may be affected by corrosion and wear and it may depend on position along the circumferential and axial direction in the pipe.

In conventional image techniques of this type, sound transmission times for use in this technique are calculated applying ray tracing techniques. However, it has been found that this leads to errors when the technique is applied to imaging of the interior of a wall of a pipe that suffers from corrosion and wear. The large difference between the sound speed in the fluid in the pipe and in the material of the pipe wall (metal for example) has the effect that minor errors in the model of the inner surface may result in large ray tracing errors. Also, the possible unevenness of the estimated surface may have the effect that inaccuracies in the ray tracing computation itself may result in large errors.

According to one aspect, it is preferred that sound transmission times are determined more efficiently applying Fermat's principle. Use of Fermat's principle comprises choosing a set of neighbouring sound transmission paths from an emitting element to a receiving element of a pair via a relevant grid point, calculating the corresponding sound transmission times and selecting the sound path with the shortest travel time for the combination of the grid point and the pair. This makes the process more robust against errors of the type that occur when the ray tracing approach is used.

Figure 2:
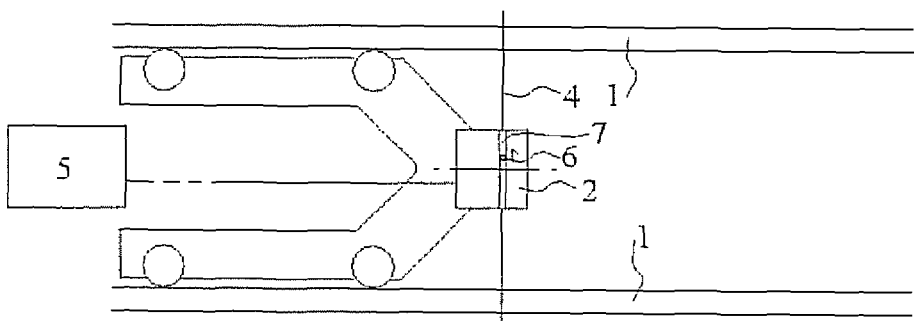
FIG. 2 shows a second embodiment of the system.

FIG. 2 shows slightly modified exemplary embodiment of a system for detecting defects in a pipe wall 1, comprising ultrasonic transducer means 2 which are arranged for emitting, via an exit opening, ultrasonic signals from the interior of the pipe towards its wall 1 and for receiving, via an entrance opening, backscattered signals from its wall 1. In this exemplary embodiment the transducer means comprise at least one ultrasonic transducer 6, and rotating or spinning (see arrow) guiding means 7 which are arranged to provide the ultrasonic signal pulses to be emitted into and the backscattered pulses to be received from all directions within the perpendicular plane 4 through the transducer means 2. The rotating guiding means 7 are preferably driven by a stepper motor (not shown explicitly) under control of the control module 5. For the rest this exemplary embodiment is similar to the embodiment of FIG. 1.

The guiding means may be a rotatable wheel on which a transducer is mounted, to guide movement of the transducer by movement of the wheel. The rotation speed of the wheel may be much slower than the speed of sound. Thus, backscatter intensity as a function of time from one transducer position substantially back to that transducer position can be obtained for series of transducer positions reached by rotating the wheel. In another embodiment, the guiding means may be a slot between two housing parts along which the transducer is guided. In this case the housing parts may also be used to apply electric potentials to the transducer along the edges of the slot. In another embodiment, the guiding means may be a rotating structure with an opening that guides the ultrasound out to the pipe wall.

Summarizing, a system for detecting defects in a pipe wall (1) is provided, comprising ultrasonic transducer means (2)

which are arranged for emitting, via an exit opening, ultrasonic signals from the interior of the pipe towards its wall and for receiving, via an entrance opening, backscattered 5 signals from its wall. In this system the transducer means are arranged to emit and receive a multitude of signals having their main directions within a plane (4) mainly perpendicular to the pipe axis. The diameter of said exit and/or entrance opening of the transducer means mainly has the magnitude of the wavelength of the used ultrasonic signals. The complex of emitted and backscattered signals is processed, in processing means (5), using a high resolution imaging process based on the transmission time of the emitted and backscattered signals.

In an embodiment the transducer means comprise a mainly circular array (3) of ultrasonic transducers, located in said plane.

In an embodiment the transducer means comprise at least one ultrasonic transducer, and guiding means (6) arranged to provide the signals to be emitted into and the backscattered pulses to be received from all directions within the perpendicular plane through the transducer means.

In an embodiment the processing means (5) comprise means for:
  a. imaging of data with a model that includes only the liquid velocity, taking into account the sound speed in the liquid within the pipe;
  b. finding the pipe's inner surface;
  c. updating the velocity model, including the sound speed in the pipe wall in the model;
  d. imaging the pipe wall, its inner and its outer surface and peculiarities like defects in the pipe wall, applying Fermat's principle on bundles of neighbouring sound transmission paths.

The invention claimed is:

1. A method of detecting defects in a pipe wall comprising
emitting ultrasonic signals from the interior of the pipe towards its wall;
receiving backscattered signals from the wall, a multitude of signals being emitted and received, having their main directions distributed within a plane perpendicular to the pipe axis;
processing the multitude of emitted and received signals, using an imaging process based on transmission times between emission and reception of the emitted and backscattered signals;
defining a grid of grid points within the pipe wall;
calculating for each grid point and for each pair of an emitting element position and a receiving element position a sound transmission time along a sound path from the emitting element position in the pair to the receiving element position in the pair, via reflection from said grid point, by choosing a set of neighboring sound transmission paths from the emitting element position to the receiving element position of the pair via said grid point, calculating the sound transmission times of the sound transmission paths and selecting the sound transmission path with the shortest travel time for the combination of the grid point and the pair; and
determining for each grid point the sum of the backscatter responses determined with different ones of the pairs at the calculated sound transmission times for the pair and the grid point.

2. A method according to claim 1, wherein an image of the pipe wall is formed by combining backscattered signals obtained for different combinations of positions of emission and reception, using the transmission times to assign backscatter intensity for the combinations to locations in the image.

3. A method according to claim 1, wherein the ultrasonic signals are transmitted via an exit opening and the ultrasonic signals are received via an entrance opening, a diameter of said exit opening and/or said entrance opening mainly having a magnitude of the wavelength of the ultrasonic signals.

4. A method according to claim 1, wherein said processing comprises imaging the pipe wall, its inner and its outer surface and peculiarities like defects in the pipe wall, applying Fermat's principle on bundles of neighboring sound transmission paths.

5. A method according to claim 1, wherein said processing comprises
  a. processing the combination of emitted and received signals to form a first backscatter image using a sound speed model that includes only a sound speed corresponding to a sound speed of in the liquid within the pipe;
  b. finding the pipe's inner surface from the first backscatter image;
  c. updating the sound speed model, including in the model the sound speed in the pipe wall bounded by the pipe's inner surface that was found from the first backscatter image;
  d. processing the combination of emitted and received signals to form a second backscatter image using the updated sound speed model.

6. A method according to claim 2, wherein the ultrasonic signals are transmitted via an exit opening and the ultrasonic signals are received via an entrance opening, a diameter of said exit opening and/or said entrance opening mainly having a magnitude of the wavelength of the ultrasonic signals.

7. A method according to claim 2, wherein said processing comprises imaging the pipe wall, its inner and its outer surface and peculiarities like defects in the pipe wall, applying Fermat's principle on bundles of neighboring sound transmission paths.

8. A method according to claim 2, wherein said processing comprises
  a. processing the combination of emitted and received signals to form a first backscatter image using a sound speed model that includes only a sound speed corresponding to a sound speed of in the liquid within the pipe;
  b. finding the pipe's inner surface from the first backscatter image;
  c. updating the sound speed model, including in the model the sound speed in the pipe wall bounded by the pipe's inner surface that was found from the first backscatter image;
  d. processing the combination of emitted and received signals to form a second backscatter image using the updated sound speed model.

9. A method according to claim 3, wherein said processing comprises imaging the pipe wall, its inner and its outer surface and peculiarities like defects in the pipe wall, applying Fermat's principle on bundles of neighboring sound transmission paths.

10. A method according to claim 3, wherein said processing comprises
  a. processing the combination of emitted and received signals to form a first backscatter image using a sound speed model that includes only a sound speed corresponding to a sound speed of in the liquid within the pipe;

b. finding the pipe's inner surface from the first backscatter image;
c. updating the sound speed model, including in the model the sound speed in the pipe wall bounded by the pipe's inner surface that was found from the first backscatter image;
d. processing the combination of emitted and received signals to form a second backscatter image using the updated sound speed model.

11. A method according to claim 5, comprising defining a grid of grid points within the pipe wall bounded by the pipe's inner surface that was found from the first backscatter image, calculating for each grid point and for each pair of an emitting element position and a receiving element position a sound transmission time along a sound path from the emitting element position in the pair to the receiving element position in the pair, via reflection from said grid point, by choosing a set of neighboring sound transmission paths from the emitting element position to the receiving element position of the pair via said grid point, calculating the sound transmission times of the sound transmission paths and selecting the sound transmission path with the shortest travel time for the combination of the grid point and the pair.

12. A system for detecting defects in a wall of a pipe from the interior of the pipe, the system comprising
at least one ultrasound transducer having an exit opening for emitting ultrasonic signals and an entrance opening for receiving backscattered signals, the at least one transducer being configured to emit and receive a multitude of signals having their main directions distributed within a plane perpendicular to an axis;
a processor, configured to process combinations of emitted and backscattered signals using an imaging process based on the transmission time between emission and reception of the emitted and backscattered signals, wherein said processor is configured to
a. define a grid of grid points within the pipe wall;
b. calculate for each grid point and for each pair of an emitting element position and a receiving element position a sound transmission time along a sound path from the emitting element position in the pair to the receiving element position in the pair, via reflection from said grid point, by choosing a set of neighboring sound transmission paths from the emitting element position to the receiving element position of the pair via said grid point, calculating the sound transmission times of the sound transmission paths and selecting the sound transmission path with the shortest travel time for the combination of the grid point and the pair;
c. determine for each grid point the sum of the backscatter responses determined with different ones of the pairs at the calculated sound transmission times for the pair and the grid point.

13. A system according to claim 12, wherein the ultrasound transducer has an exit opening and/or an entrance opening, a diameter of said exit opening and/or said entrance opening of the transducer having a magnitude of at most twice a wavelength of ultrasound at a transmission frequency of the transducer.

14. A system according to claim 12, comprising a circular array of ultrasonic transducers, located in said plane.

15. A system according to claim 12, comprising guiding means arranged to provide the signals to be emitted into and the backscattered pulses to be received from all directions within the perpendicular plane through the transducer.

16. A system according to claim 12, wherein said processor is configured to
a. image data with a model that includes only the liquid velocity, taking into account the sound speed in the liquid within the pipe;
b. find the pipe's inner surface;
c. update the velocity model, including the sound speed in the pipe wall in the model;
d. image the pipe wall, its inner and its outer surface and peculiarities like defects in the pipe wall, applying Fermat's principle on bundles of neighboring sound transmission paths.

17. A computer readable medium comprising a program of instructions for a programmable computer, which when executed by a programmable computer will cause the computer to operate as the processor in claim 12.

18. A system according to claim 13, comprising the pipe, the ultrasound transducer having the exit opening in the interior of the pipe arranged to emit the ultrasonic signals towards the pipe wall and the entrance opening arranged to receive ultrasonic signals backscattered signals from the pipe wall.

* * * * *